US011478499B2

(12) United States Patent
Van Aken et al.

(10) Patent No.: US 11,478,499 B2
(45) Date of Patent: Oct. 25, 2022

(54) COMPOSITIONS FOR USE TO TREAT CATARACT

(71) Applicants: Universiteit Gent, Ghent (BE); VIB VZW, Zwijnaarde (BE)

(72) Inventors: Elisabeth Van Aken, Heusden (BE); Joris Delanghe, Aalst (BE); Nico Callewaert, Deinze (BE); Loes Van Schie, Ghent (BE)

(73) Assignees: Universiteit Gent, Ghent (BE); VIB VZW, Zwijnaarde (BE)

(*) Notice: Subject to any disclaimer, the term of this patent is extended or adjusted under 35 U.S.C. 154(b) by 257 days.

(21) Appl. No.: 16/964,149

(22) PCT Filed: Jan. 28, 2019

(86) PCT No.: PCT/EP2019/051961
§ 371 (c)(1),
(2) Date: Jul. 22, 2020

(87) PCT Pub. No.: WO2019/149648
PCT Pub. Date: Aug. 8, 2019

(65) Prior Publication Data

US 2021/0030780 A1 Feb. 4, 2021

(30) Foreign Application Priority Data

Jan. 30, 2018 (EP) .................................... 18154064

(51) Int. Cl.
*A61K 31/7076* (2006.01)
*A61K 33/06* (2006.01)
*A61K 38/45* (2006.01)
*A61K 9/00* (2006.01)

(52) U.S. Cl.
CPC .......... *A61K 31/7076* (2013.01); *A61K 33/06* (2013.01); *A61K 38/45* (2013.01); *C12Y 207/01171* (2013.01); *A61K 9/0019* (2013.01); *A61K 9/0048* (2013.01)

(58) Field of Classification Search
CPC .... A61K 31/7076; A61K 33/06; A61K 38/45; A61K 9/0019; A61K 9/0048; A61K 45/06; C12Y 207/01171; A61P 27/12
See application file for complete search history.

(56) References Cited

FOREIGN PATENT DOCUMENTS

WO 2017/078953 A1 5/2017

OTHER PUBLICATIONS

Li et al., Appl. Biochem. Biotechnol., 2007, 142, p. 104-124. (Year: 2007).*
Dunmore et al., Diabetes, 2018, 67, p. 131-136. (Year: 2018).*
Agarwal et al "Current and effective advantages of femto phacoemulsification" Curr Opin Ophthalmol 2017;28:49-57 DOI: 10.1097/ICU.0000000000000333.
Andexer et al "Emerging Enzymes for ATP Regeneration in Biocatalytic Processes". ChemBioChem 2015, 16, 380-386, DOI: 10.1002/cbic.201402550.
Ávila et al. "Photosensitized reactions mediated by the major chromophore arising from glucose decomposition, result in oxidation and cross-linking of lens proteins and activation of the proteasome" Biochimica et Biophysica Acta 1822(2012) 564-572.
Delpierre et al. "Fructosamine 3-kinase is involved in an intracellular deglycation pathway in human erythrocytes", Biochem. J. (2002) 365, 801-808.
Delpierre et al. "Identification, cloning, and heterologous expression of a mammalian fructosamine-3-kinase" Diabetes; Oct. 2000, vol. 49, pp. 1627-1634.
Dillon et al. "The photochemical attachment of the O-glucoside of 3-hydroxykynurenine to alpha-crystallin: a model for lenticular aging" Photochemistry and Photobiology, 1999; 69(2), pp. 248-253.
Favre et al. "Reactivation of Creatine Kinase by Dithiothreitol Prior to Use in an In Vitro Translation Extract" ALTEX 22, 259-264.
Halfter et al. "Embryonic Synthesis of the Inner Limiting Membrane and Vitreous Body" Invest Ophthalmol Vis Sci, Jun. 2005, vol. 46, No. 6, pp. 2202-2209.
Hayer-Hartl "Assay of Malate Dehydrogenase" Methods in Molecular Biology, vol. 140: Chaperonin Protocols, pp. 127-132. Springer, Totowa, NJ Available at: https://link.springer.com/protocol/10.1385/1-59259-061-6:127 [Accessed Nov. 26, 2017].
Hellwig et al. "A new HPLC-based assay for the measurement of fructosamine-3-kinase (FN3K) and FN3K-related protein activity in human erythrocytes" DOI 10.1515/cclm-2012-0853 Clin Chem Lab Med 2014; 52(1): 93-101.
Liu et al. "Cataracts" Lancet 2017; vol. 390: (600-12) Aug. 5, 2017.
Pescosolido et al. "Age-related changes in the kinetics of human lenses: prevention of the cataract" Int J Ophthalmol, 2016;9(10):1506-1517.
Rosenfield et al. for the MARINA Study Group "Ranibizumab for Neovascular Age-Related Macular Degeneration" N Engl J Med 2006;355:1419-31.
Shiels et al. "Genetics of human cataract" JF. Genetics of human cataract. Clin Genet 2013; 84:120-127.
Szwergold et al. "Human Fructosamine-3-Kinase Purification, Sequencing, Substrate Specificity, and Evidence of Activity In Vivo" DIABETES, vol. 50, Sep. 2001, 2139-2147.
Woodyer et al. "Regeneration of Cofactors for Enzyme Biocatalysis" Enzyme Technology; Springer Science+Business Media,Inc. and Asiatech Publishers, Inc., 2006, pp. 83-101.
World Health Organization "Blindness and vision impairment prevention" Priority Eye Diseases Accessed Aug. 12, 2020, at https://www.who.int/blindness/causes/priority/en/index1.html.
Avemaria et al "Possible role of fructosamine 3-kinase genotyping for the management of diabetic patients" Clinical Chemistry and Laboratory Medicine,, vol. 53. No. 9 (Jan. 2015) pp. 1315-1320.

(Continued)

*Primary Examiner* — Jonathan S Lau
(74) *Attorney, Agent, or Firm* — TraskBritt

(57) ABSTRACT

A non-surgical treatment of cataract in a human or animal. The invention specifically relates to the administration of a deglycating enzyme and its cofactor(s), which results in the deglycation of the lens crystallins. The disclosure thus relates to a minimal invasive type of treatment of cataract, which is easier and cheaper compared to existing surgical methods.

19 Claims, 8 Drawing Sheets

Specification includes a Sequence Listing.

(56) References Cited

OTHER PUBLICATIONS

Dilsiz et al. "Determination of Calcium, Sodium, Potassium and Magnesium Concentrations in Human Senile Cataractous Lenses" Cell Biochem Funct. 18 (Dec. 2000) pp. 259-262.
International Search Report for International Application No. PCT/EP2019/051961, dated Apr. 10, 2019, 4 pages.
International Written Opinion for International Application No. PCT/EP2019/051961, dated Apr. 10, 2019, 6 pages.
Japanese Notice of Reasons for Refusal for Japanese Application No. 2020-562841, dated Jun. 1, 2022, 9 pages with English translation.
Minnaert et al. "Yeast-produced fructosamine-3-kinase retains mobility after intravitreal injection and topical application in human and bovine eyes as determined by fluorescence correlation spectroscopy" Int J Pharmaceutics 621: 121772 (Jun. 2022).
Popova et al., "Non-Enzymatic Glycosylation and Deglycating Enzymes", Biotechnology & Biotechnological Equipment, vol. 24. No. 3 (Jan. 2010).
Schoonooghe et al. "Efficient production of human bivalent and trivalent anti-MUCI Fab-scfv antibodies in Pichia pastoris" BMC Biotechnology, Research Article, 9:70 (Aug. 2009) 14 pages.
Szwergold "Fructose-3-phosphate (F3P) Inhibits the Phosphorylation of Protein-bound Fructoselysine by Fructosamine-3-kinase (FN3K)" IOVS, vol. 44, Issue 13 (May 2003).

* cited by examiner

Mouse 832 ob/ob

Untreated (saline water)

Ratio x/y = 0.6

Treated (FN3K)

Ratio x/y = 1.0

Mouse 814 ob/ob

Untreated (ATP-$MgCl_2$)

Ratio x/y = 0.9

Treated (FN3K)

Ratio x/y = 1.0

COMPOSITIONS FOR USE TO TREAT CATARACT

CROSS-REFERENCE TO RELATED APPLICATIONS

This application is a national phase entry under 35 U.S.C. § 371 of International Patent Application PCT/EP2019/051961, filed Jan. 28, 2019, designating the United States of America and published in English as International Patent Publication WO 2019//149648 A1 on Aug. 8, 2019, which claims the benefit under Article 8 of the Patent Cooperation Treaty to European Patent Application Serial No. 18154064.2, filed Jan. 30, 2018.

TECHNICAL FIELD

The application relates to a non-surgical treatment of cataract in a human or animal. The disclosure specifically relates to the administration of a deglycating enzyme and its cofactor(s), which results in the deglycation of the lens crystallins. The disclosure thus relates to a minimal invasive type of treatment of cataract, which is easier and cheaper compared to the existing surgical methods.

BACKGROUND

Cataract is a global public health problem. Due to the global increase of life expectancy, prevalence of cataract is rising in both industrialized and third world countries. An estimated 95 million people worldwide are affected by cataract (1). Cataract is still the major cause of blindness in the (developing) world (20 million people affected according to the World Health Organization (WHO)) (2). In 2012, over 120,000 cataract operations have been performed in Belgium alone and this number is still increasing every year. As current surgical cataract treatment is relatively expensive and the number of practicing ophthalmologists is small in many developing countries, there is a growing demand for affordable cataract prevention or treatment, which is accessible to a larger amount of patients. In the western world, cataract is treated by a surgical intervention by a trained ophthalmologist, called phacoemulsification (3). This method consists of the fragmentation of the intraocular cataractous lens by ultrasound waves and replacing the latter by a new silicone or acrylic lens implant. However, major drawbacks of this surgical technique are the high financial costs (surgical machinery (cost 40,000-50,000 Euro), operation microscope (cost 50,000-70,000 Euro), machinery for calculating the lens implant (15,000-20,000 Euro), reimbursement by national health insurance between 1,500 and 2,500 Euro per surgery per eye in one-day surgery), a long learning curve of several years for the ophthalmic surgeon, the risk of postoperative vision-threatening endophthalmitis, and still the need of reading glasses afterwards (unless multifocal lenses are implanted, which cost 1,000 to 1,500 Euro and are not affordable by most patients). At the time being, the room for improvement of current treatment strategies is marginal and is mainly focusing on improving the quality of the implanted lenses.

The crystalline lens is a transparent biconvex structure in the eye. a-, b- and g-crystallins make up >90% of the total dry mass of the lens (4). Due to a very low protein turnover, crystallins belong to the longest-lived proteins in the body and are therefore prone to progressive glycation with age. In the process of protein glycation, metabolically important sugars such as glucose and fructose react with primary amine groups (amino-terminus and e-aminogroup of lysine), forming adducts that can then rearrange and react further, eventually leading to cross-links between proteins, which often inactivates these proteins or makes them resistant to the natural cellular degradation machinery. This process in which these Advanced Glycation End products (AGEs) are formed is also more generally known as the "Maillard" reaction, which is in fact a very complex and as yet quite incompletely understood set of reactions. Non-enzymatic glycation and oxidative damage of lens proteins are the major factors responsible for cataract formation, by altering the lens protein structure and stability and inducing protein cross-linking, aggregation and insolubilization. Dillon et al. (5) highlighted the possible role of the Maillard reaction in lenticular protein glycation. Because of the long half-life, crystallin undergoes irreversible posttranslational modifications, of which glycation is prominent especially in ageing and diabetes mellitus. Recently, a large spectrum of AGEs was quantitated with liquid chromatography-tandem mass-spectrometry. AGEs induce structural changes, that affect lens transparency. In the eye lenses from young patients, only 1.3% of the lysine residues of crystallins are glycated, while at 50 years of age this value increases from 2.7% to about 4.2% in old people. In advanced stages of the Maillard reaction, sugar residues can further cross-link with other proteins of the lens. In fact, brown pigments isolated from cataract after proteolytic digestion have an UV rays absorption spectrum, a fluorescence excitation spectrum and a chromatographic retention timing similar to the products of the Maillard reaction (6). The proportion of AGEs is even more substantial in diabetic patients, as the chronically elevated glucose concentration in hyperglycemia speeds up the production of AGEs. Concomitantly, the prevalence of cataract in diabetic patients is fivefold higher than among non-diabetics. Cataract is indeed the major complication in diabetic patients even in young persons: 23-26% of diabetic patients <54 years old show cataract, compare to 4-7% in non-diabetic individuals of the same age group. This percentage increases with age: in the age group of 55-64 years old persons, cataract can be detected in 54-70% of diabetic patients and in 31-45% of non-diabetic individuals (7).

The enzyme fructosamine-3-kinase has long been known to constitute part of the natural cellular repair capacity for the initial condensation product of glucose with protein primary amine groups (8). Its requirement for ATP as a co-substrate means that it requires a cellular context to work, and this has discouraged investigations with regard to potential therapeutic use. More importantly, the enzymes action on advanced glycation end products (AGEs) is unknown.

The vitreous body of the eye is a perfect reservoir for containing therapeutic agents in treating retinal diseases, as has already extensively been shown through the past 10 years. Anti-Vascular Endothelial Growth Factor antibodies (ranibizumab, bevacizumab), Vascular Endothelial Growth Factor decoy receptors (aflibercept), have been injected routinely into the vitreous for the treatment of macular edema and hemorrhages due to diabetic retinopathy, retinal vein occlusion, age-related macular degeneration, pathologic myopia since 2006 (9). The vitreous body is located between the eye lens and the retina and consists of an essentially acellular viscoelastic gel that contains more than 98% water and 2% hyaluronic acid, collagens type II and IX, fibronectin, fibrillin and opticin (10).

It is however completely unknown whether local application-via a single intravitreal injection-of a deglycating enzyme such as fructosamine-3-kinase and it required cofactor(s) would result in the disruption of the Advanced Glycation End products and cross-linked structures, which leads to clearing and softening of the lens and hence the treatment of cataract.

BRIEF DESCRIPTION OF THE DRAWINGS

FIG. 7 shows human cataract lens fragment pool samples treated with a solution of 16 pg/ml FN3K, 4 mM $MgCl_2$ and 0, 0.125, 0.25 or 2.5 mM ATP in saline, either as such or supplemented with an ATP regeneration system consisting of 20 mM phosphocreatine (Sigma) and 0.5 mg/ml creatine kinase from rabbit muscle (Sigma). Fluorescence spectra were recorded with the 365 nm excitation intensity set as such that the detected 365 nm peak (excitation beam) was equally high in each condition measured, allowing comparison of spectra.

DETAILED DESCRIPTION

Figure 1:
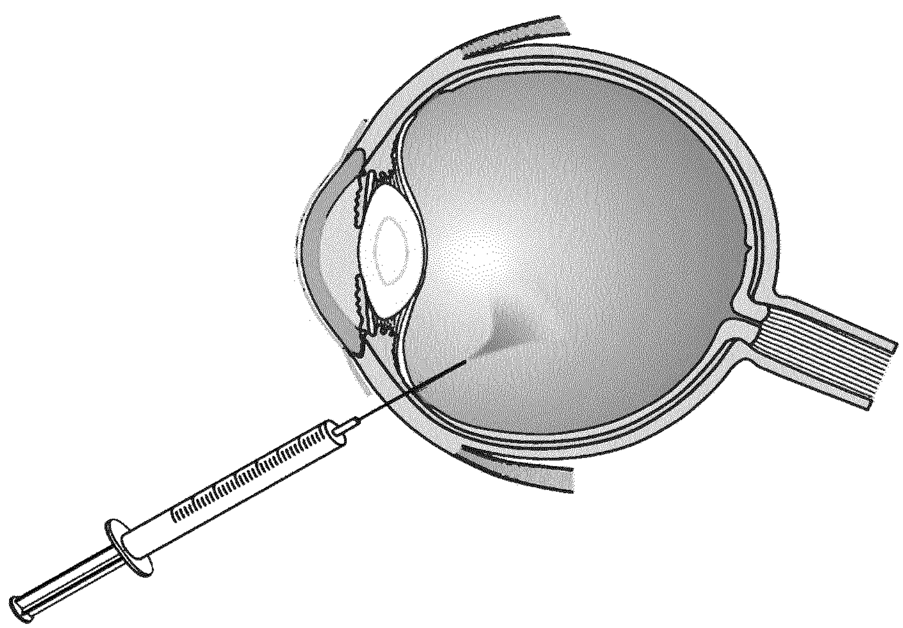
FIG. 1 illustrates a system for intravitreal injecting deglycating enzymes according to an embodiment of the disclosure.

The disclosure relates to the surprising finding that administration, such as by a single intravitreal injection, of a fructosamine-3-kinase and its co-factor(s) results in "cleaning" of heavily glycated and cross-linked lenses and affects their mechanical properties. In other words, the latter administration/injection restores light transmission of the lenses and can thus be used to treat cataract or prevent the development of cataract.

The disclosure thus in first instance relates to a composition comprising a fructosamine-3-kinase and adenosine tri phosphate for use to treat cataract in a human or an animal.

The disclosure further relates to a composition comprising a fructosamine-3-kinase and adenosine tri phosphate for use to treat cataract in a human or an animal wherein the composition is administered by intravitreal injection.

The disclosure further relates to a composition for use as described above, which composition further comprises magnesium ions and/or an adenosine tri-phosphate regenerating system.

The disclosure further relates to a composition comprising a fructosamine-3-kinase and adenosine tri-phosphate regenerating system for use to treat cataract(s) in a human or an animal.

The disclosure further relates to a composition comprising a fructosamine-3-kinase and adenosine tri-phosphate regenerating system for use to treat cataract(s) in a human or an animal wherein the composition is administered by intravitreal injection.

The disclosure further relates to a composition comprising a fructosamine-3-kinase and adenosine tri phosphate regenerating system for use as described above which further comprises magnesium ions.

The term "a fructosamine-3-kinase" relates to enzymes classified as enzymes 2.7.1.171 in, for example, the Brenda enzyme database (www.brenda-enzymes.org). The latter enzymes are part of an ATP-dependent system for removing carbohydrates from non-enzymatically glycated proteins and catalyze the following reaction: ATP+[protein]-N6-D-fructosyl-L-lysine=ADP+[protein]-N6-(3-0-phospho-D-fructosyl)-L-lysine. More specifically, the term "a fructosamine-3-kinase" relates to—as a non-limiting example—to the human fructosamine-3-kinase having accession number or the National Center for Biotechnology Information ("NCBI") Reference sequence number:NP 071441.1 (see www.ncbi.nlm.nih.gov/protein/NP 071441). It should be further clear that the term "a fructosamine-kinase" relates to the enzymes as described above, but also to functional fragments and variants thereof. The term "functional fragments and variants" relates to fragments and variants of the naturally occurring enzymes. Indeed, for many applications of enzymes, part of the protein may be sufficient to achieve an enzymatic effect. The same applies for variants (i.e., proteins in which one or more amino acids have been substituted with other amino acids, but which retain functionality or even show improved functionality), in particular, for variants of the enzymes optimized for enzymatic activity (as is also described further with regard to recombinant enzymes). The term "fragment" thus refers to an enzyme containing fewer amino acids than the 309 amino acid sequence of the human fructosamine-3-kinase having NCBI Reference sequence number: NP_071441.1 and that retains the enzyme activity. Such fragment can, for example, be a protein with a deletion of 10% or less of the total number of amino acids at the C- and/or N-terminus. The term "variant" thus refers to a protein having at least 50% sequence identity, preferably having at least 51-70% sequence identity, more preferably having at least 71-90% sequence identity or most preferably having at least 91, 92, 93, 94, 95, 96, 97, 98 or 99% sequence identity with the 309 amino acid sequence of the human fructosamine-3-kinase having NCBI Reference sequence number:NP_071441.1 and that retains the enzyme activity.

Hence, orthologues, or genes in other genera and species (than the human fructosamine-3-kinase having NCBI Reference sequence number:NP_071441.1) with at least 50% identity at amino acid level, and having the enzyme activity are part of the disclosure. The percentage of amino acid sequence identity is determined by alignment of the two sequences and identification of the number of positions with identical amino acids divided by the number of amino acids in the shorter of the sequences×100. The latter "variant" may also differ from the protein having NCBI Reference sequence number:NP_071441.1 only in conservative substitutions and/or modifications, such that the ability of the protein to have enzymatic activity is retained. A "conservative substitution" is one in which an amino acid is substituted for another amino acid that has similar properties, such that one skilled in the art of protein chemistry would expect the nature of the protein to be substantially unchanged. In general, the following groups of amino acids represent conservative changes: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his.

Variants may also (or alternatively) be proteins as described herein modified by, for example, the deletion or addition of amino acids that have minimal influence on the enzymes activity as defined above, secondary structure and hydropathic nature of the enzyme.

The terms "adenosine tri-phosphate" (ATP) and "magnesium ions" relate to well-known cofactors of the latter enzymes.

The term "adenosine tri-phosphate generating system" relates to several enzymatic and whole-cell based methods to regenerate ATP from ADP or AMP as are, for example, described by Woodyer R. D. et al. 2006 (11). In particular, the latter term refers to the following four enzymes commonly used in the regeneration of ATP from ADP: 1) the use of phosphoenolpyruvate in a coupled reaction catalyzed by pyruvate kinase, 2) acetylphosphate coupled with acetate kinase, 3) creatine phosphate coupled with creatine kinase, and 4) polyphosphate coupled with polyphosphate kinase. Preferably, the term "ATR generating system" refers to the usage of phosphocreatine as a secondary energy source and creatine kinase to transfer its phosphate group to ADP to regenerate ATP. The usage of the latter ATP generating systems thus limits the concentration of ATP present in the mixture injected into the vitreous body as is also described further.

The terms "to treat cataract" relate to restoring light transmission and/or improving mechanical properties such as elasticity of the lenses in order to improve vision of the treated subject. The latter term may also relate to preventing further deterioration of the light transmission and/or mechanical properties of a lens. In other words, the term treatment involves a deglycation of lens proteins resulting in clearing and softening of the lens.

The term "animal" may relate to any animal such as a horse, pig, sheep, dog, cat or mouse.

The terms "administration by intravitreal injection" relate to injection of the compounds of the disclosure into the vitreous body of the eye. The intravitreal injection technique is used under controlled aseptic conditions. Adequate anesthesia is given prior to the injection. For the treatment of animal eyes, general anesthesia is used by, for example, inhalation anesthesia with isoflurane 5%. For the treatment of, e.g., humans, local anesthetic drops can be used. A 32-gauge needle can be used for injection in smaller animal (such as a small rodent) eyes and a 30-gauge needle in human eyes and eyes of bigger animals such as horse and pig. In all species, the sclera is penetrated at an angle from 45°-90°. In mice, for example, the sclera can be penetrated at 1-1.5 millimeter from the limbus, and in humans the sclera can be penetrated at 3-5 millimeter from the limbus. The needle passes through the sclera and choroid until the vitreous body is reached. The needle does not touch the lens, nor the retina. The composition of the disclosure can be as such delivered and the needle is withdrawn immediately.

However, it should be clear that besides injecting the therapeutically effective amounts intravitreally-which is the preferred way of administration-also other means of administration could be envisioned such as—but not limited to—external application such as drops or gels, other internal applications such as suprachoroidal delivery, subretinal delivery, delivery by gene therapy by the use of adeno-associated viruses or other viruses, or, implants with or without possibility to refill in the vitreous, everywhere else in the eye or eye adnexa.

The disclosure thus relates—in other words—to a method to treat (or prevent) cataract in a subject in need thereof wherein the method comprises an injection (or administration) of a therapeutically effective amount of a compound comprising a fructosamine-3-kinase and adenosine tri phosphate, or, a fructosamine-3-kinase and an adenosine tri phosphate generating system, or, a fructosamine-3-kinase and adenosine tri phosphate and an adenosine tri phosphate generating system, or a fructosamine-3-kinase and adenosine tri phosphate and magnesium ions, or, a fructosamine-3-kinase and adenosine tri phosphate and an adenosine tri phosphate generating system and magnesium ions, or, a fructosamine-3-kinase and an adenosine tri phosphate generating system and magnesium ions in the vitreous body of the eye of the subject.

The term "a therapeutically effective amount" relates to an amount ranging from 5 ml (for injecting into a single mouse eye) to 50 ml (for injecting into a single bovine eye) taken from a therapeutic dose ranging between about 4.17 and 12.5 pg/ml fructosamine-3-kinase, 2.50 and 4.17 mM ATP and 1.00 and 1.67 mM $MgCl_2$. The latter therapeutic doses can be obtained by mixing 1:1, 1:2, 1:3 or 1:5 a solution of 25 pg/ml fructosamine-3-kinase with a fresh solution of 5 mM ATP/2 mM $MgCl_2$.

The disclosure further relates to a composition as indicated above wherein the fructosamine-3-kinase is a recombinant fructosamine-3-kinase. The term “recombinant” refers to fructosamine-3-kinase obtained as an outcome of the expression of recombinant DNA encoding for a fructosamine-3-kinase inside living cells such as bacteria or yeast cells. Practitioners are further directed to Sambrook et al. Molecular Cloning: A laboratory Manual, 4th ed., Cold Spring Harbor press, Plainsview, New York (2012) and Ausubel et al. Current Protocols in Molecular Biology (supplement 114), John Wiley & Sons, New York (2016).

More specifically, the disclosure relates to a recombinant fructosamine-3-kinase, which is obtainable by recombinant production in *Pichia pastoris* and, even more specifically, wherein the recombinant fructosamine-3-kinase obtainable by recombinant production in *Pichia pastoris* has the amino acid sequence as given by SEQ ID NO: 1 or SEQ ID NO:2. SEQ ID NO:1 is a construct with an N-terminal cleavable HIS-tag and a caspase 3-cleavable Asp-Glu-Val-Asp (DEVD) linker between the His6 tag and the protein coding sequence, which allows for clean removal of the tag. SEQ ID NO: 2 is the cleaved version of SEQ ID NO:1.

The amino acid sequences of SEQ ID NO:1 and SEQ ID NO:2 (and their encoding nucleic acid sequences SEQ ID N3 and SEQ ID NO: 4, respective) are as follows:

```
SEQ ID NO: 1:
Type: amino acid 1-letter (underlined: His6-tag. italics: linker,
bold underlined: caspase cleavage site)
MHHHHHH WVGPGSDEVDEQLLRAELRTATLRAFGGPGAGCI
SEGRAYDTDAGPVFVKVNRRTQARQMF
EGEVASLEALRSTGLVRVPRPMKVIDLPGGGAAFVMEHLKMKSLSSQASKLGEQ
MADLHLYNQKLREK
LKEEENTVGRRGEGAEPQYVDKFGFHTVTCCGFIPQVNEWQDDWPTFFARHRL
QAQLDLIEKDYADRE
ARELWSRLQVKIPDLFCGLEIVPALLHGDLWSGNVAEDDVGPI
IYDPASFYGHSEFELAIALMFGGFP
RSFFTAYHRKIPKAPGFDQRLLLYQLFNYLNHWNHFGREYRSPSLGTMRRLLK*

SEQ ID NO: 3:
Type: DNA (underlined: His6-tag. italics: linker, bold underlined:
caspase cleavage site)
ATGCATCATCATCATCATCAT
rrAACGGrCCAGGrrCTGATGAAGTTGATGAACAGTTGTTGAGAGC
TGAGTTGAGAACTGCTACTTTGAGAGCTTTTGGTGGTCCAGGTGCTGGTTGTA
TTTCTGAGGGTAGAG
CTTACGATACTGACGCTGGTCCAGTTTTCGTTAAGGTTAACAGAAGAACTCAG
GCTAGACAGATGTTC
GAGGGTGAAGTTGCTTCTTTGGAGGCTTTGAGATCCACTGGTTTGGTTAGAGT
TCCAAGACCAATGAA
GGTTATCGACTTGCCAGGTGGTGGTGCTGCTTTTGTTATGGAACACTTGAAGA
TGAAGTCCTTGTCCT
CCCAGGCTTCTAAGTTGGGTGAACAAATGGCTGACTTGCACTTGTACAACCA
GAAGTTGAGAGAAAAG
TTGAAAGAGGAAGAGAACACTGTTGGTAGAAGAGGTGAAGGTGCTGAGCCA
CAATACGTTGACAAGTT
CGGTTTCCACACTGTTACTTGTTGTGGTTTCATCCCACAGGTTAACGAGTGGC
AAGATGACTGGCCAA
CTTTCTTCGCTAGACACAGATTGCAAGCTCAGTTGGACTTGATCGAGAAGGA
CTACGCTGACAGAGAA
GCTAGAGAATTGTGGTCCAGATTGCAGGTTAAGATCCCAGACTTGTTCTGTGG
TTTGGAGATCGTTCC
AGCTTTGTTGCACGGTGATTTGTGGTCTGGTAACGTTGCTGAAGATGACGTTG
GTCCAATTATCTACG
ACCCAGCTTCTTTCTACGGTCACTCTGAATTCGAGTTGGCTATCGCTTTGATGT
TCGGTGGTTTCCCA
AGATCCTTCTTCACTGCTTACCACAGAAAGATCCCAAAGGCTCCAGGTTTCGA
CCAGAGATTGTTGTT
GTACCAGTTGTTCAACTACTTGAACCATTGGAACCACTTCGGTAGAGAGTAC
AGATCTCCATCCTTGG
GTACTATGAGAAGATTGTTGAAGTAA

SEQ ID NO: 2 (= FN3K after N-terminal HIS-tag removal):
Type: amino acid 1-letter
EQLLRAELRTATLRAFGGPGAGCISEGRAYDTDAGPVFVKVNRRTQARQMFEGE
VASLEALRSTGLVR
VPRPMKVIDLPGGGAAFVMEHLKMKSLSSQASKLGEQMADLHLYNQKLREKLK
EEENTVGRRGEGAEP
QYVDKFGFHTVTCCGFIPQVNEWQDDWPTFFARHRLQAQLDLIEKDYADREAR
ELWSRLQVKIPDLFC GLEIVPALLHGDLWSGNVAEDDVGP I
IYDPASFYGHSEFELAIALMFGGFPRSFFTAYHRKIPKAPGF
DQRLLLYQLFNYLNHWNHFGREYRSPSLGTMRRLLK*

SEQ ID NO: 4:
Type: DNA
GAACAGTTGTTGAGAGCTGAGTTGAGAACTGCTACTTTGAGAGCTTTTGGTG
GTCCAGGTGCTGGTTG
TATTTCTGAGGGTAGAGCTTACGATACTGACGCTGGTCCAGTTTTCGTTAAGG
TTAACAGAAGAACTC
```

-continued

```
AGGCTAGACAGATGTTCGAGGGTGAAGTTGCTTCTTTGGAGGCTTTGAGATC
CACTGGTTTGGTTAGA
GTTCCAAGACCAATGAAGGTTATCGACTTGCCAGGTGGTGGTGCTGCTTTTGT
TATGGAACACTTGAA
GATGAAGTCCTTGTCCTCCCAGGCTTCTAAGTTGGGTGAACAAATGGCTGACT
TGCACTTGTACAACC
AGAAGTTGAGAGAAAAGTTGAAAGAGGAAGAGAACACTGTTGGTAGAAGAG
GTGAAGGTGCTGAGCCA
CAATACGTTGACAAGTTCGGTTTCCACACTGTTACTTGTTGTGGTTTCATCCC
ACAGGTTAACGAGTG
GCAAGATGACTGGCCAACTTTCTTCGCTAGACACAGATTGCAAGCTCAGTTG
GACTTGATCGAGAAGG
ACTACGCTGACAGAGAAGCTAGAGAATTGTGGTCCAGATTGCAGGTTAAGAT
CCCAGACTTGTTCTGT
GGTTTGGAGATCGTTCCAGCTTTGTTGCACGGTGATTTGTGGTCTGGTAACGT
TGCTGAAGATGACGT
TGGTCCAATTATCTACGACCCAGCTTCTTTCTACGGTCACTCTGAATTCGAGT
TGGCTATCGCTTTGA
TGTTCGGTGGTTTCCCAAGATCCTTCTTCACTGCTTACCACAGAAAGATCCCA
AAGGCTCCAGGTTTC
GACCAGAGATTGTTGTTGTACCAGTTGTTCAACTACTTGAACCATTGGAACCA
CTTCGGTAGAGAGTA
CAGATCTCCATCCTTGGGTACTATGAGAAGATTGTTGAAGTAA
```

The disclosure indeed relates—in addition—to the finding that the recombinant fructosamine-3-kinase obtainable by recombinant production in *Pichia pastoris* and having the amino acid sequence as given by SEQ ID NO: 1 and 2 are preferred enzymes for treating cataract. Indeed, the latter enzymes are preferred as 1) their production in *Pichia* resulted in higher yields of the enzyme compared with the production in, for example, E. coli, 2) the enzymes had a higher purity when analyzed on SDS page, and 3) the presence of endotoxin, which is known to provoke an ocular inflammation during intravitreal injection (ref), can be avoided.

The following examples are provided to better illustrate the disclosure and should not be considered as limiting the scope of the invention.

Example 1

Recombinant Production of Fructosamine-3-kinase

A gene coding for human fructosamine-3-kinase (having accession number or the National Center for Biotechnology Information (NCBI) Reference sequence number: NP_071441.1 (see www.ncbi.nlm.nih.gov/protein/NP 071441), codon-optimized for *Pichia pastoris* expression (SEQ ID NO: 1), was cloned into the pKai61 *P. pastoris* expression vector according to Claes, K. et al. ("Modular Integrated Secretory System Engineering in *Pichia Pastoris* To Enhance G-Protein Coupled Receptor Expression," ACS Synthetic Biology 5, no. 10 (Oct. 21, 2016): 1070-75). The encoded gene contains an N-terminal His6-tag (MHHHHHH) in frame with a caspase-3 cleavage site (DEVD) and the expression is under control of the methanol inducible AOX1 promoter. The plasmid contains a Zeocin™ resistance marker for selection in bacterial as well as in yeast cells. The vectors were linearized in the AOX1 promoter before transformation to *P. pastoris* (strain NRRL Y-11430) to promote homologous recombination in the endogenous AOX1 locus for stable integration into the genome.

Stable integrants were grown shaking at 28° C. in BMY buffered complex medium (10 g/L yeast extract, 20 g/L peptone, 100 mM potassium phosphate buffer pH 6.0, 13.4 g/L YNB without amino acids) complemented with 1% glycerol. After 48 hours of growth, recombinant expression was induced by transfer to BMY medium complemented with 1% methanol. After 48 hours of expression, cultures were centrifuged, supernatant was discarded and pellets were flash frozen in liquid nitrogen and stored at −20° C.

Pellets were thawed and re-suspended in washing buffer for protein extraction. *Pichia pastoris* cells were mechanically disrupted using 0.5 mm glass or silicia/zirkonium beads. The cleared supernatant was purified by $Ni^{2+}$ affinity chromatography for the His6-tagged fructosamine-3-kinase, followed by gel filtration. The protein eluted in FN3K sample buffer (20 mM Tris-HCI pH 8.0, 150 mM NaCl, 1 mM DTT) was identified as recombinant human fructosamine-3-kinase by SDS-PAGE and Western blotting with antibodies against the His6-tag and human FN3K (ThermoFisher). Enzymatic activity was confirmed in a kinase activity assay with a 1 deoxy 1 morpholino D fructose substrate (R&D Systems). Fructosamine-3-kinase aliquots were flash frozen in liquid nitrogen and stored at −20° C.

Example 2

Figure 2A:
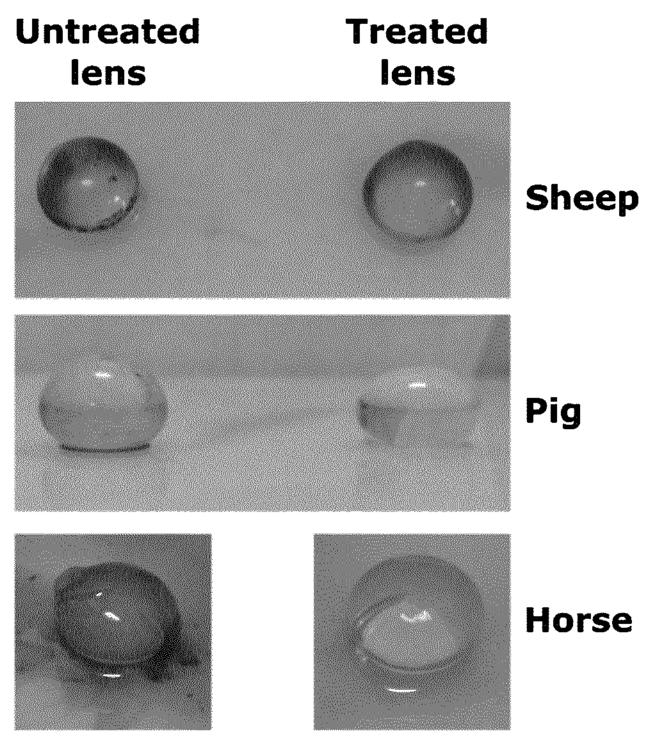
FIG. 2*a* shows the macroscopic changes of ovine, porcine and equine lenses observed following overnight treatment with intravitreal injection of fructosamine-3 kinase and magnesium chloride/adenosine triphosphate. Untreated (left figure) and fructosamine-3-kinase treated (right figure) eye lenses are shown.
Figure 3:
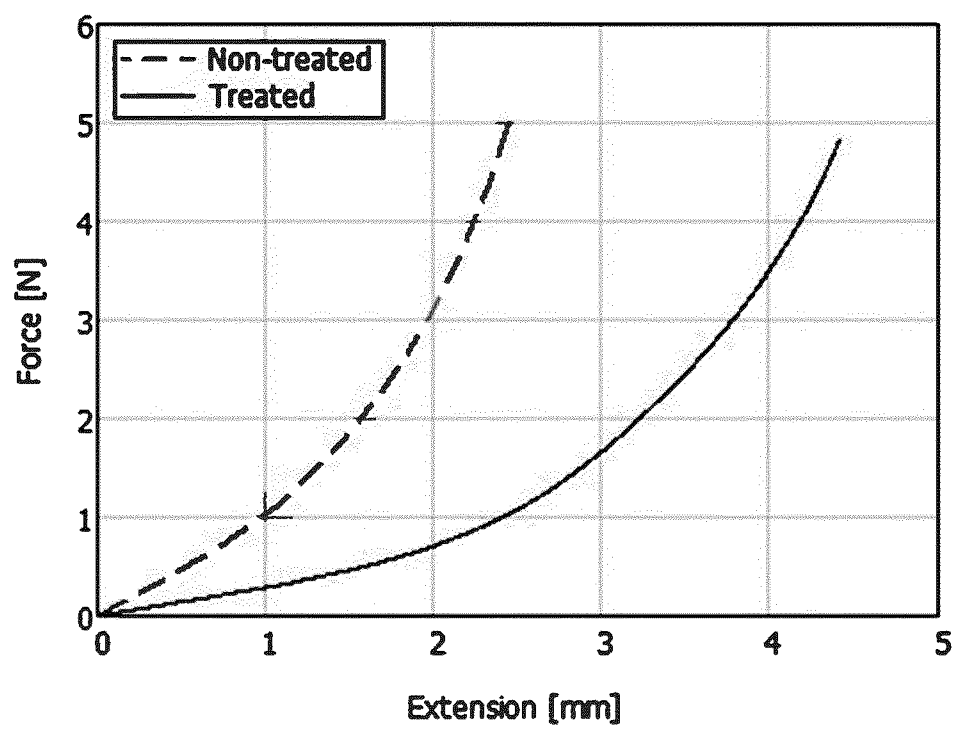
FIG. 3 illustrates the change in mechanical properties of an equine eye lens following enzymatic treatment with fructosamine-3 kinase, according to an embodiment of the disclosure. Extension rate of an untreated (dashed line) and a treated (full line) equine eye lens is shown.

Macroscopic changes of lenses of pig, sheep and horse observed following overnight treatment with intravitreal injection of fructosamine-3 kinase. The two eyes of the same animal were eviscerated and compared to have the best comparable material possible. Pig, sheep and horse eyes were eviscerated from fresh cadavers and transported to the lab on ice before injection. One eye was injected with 50 ml of a solution containing 8.33 pg/ml recombinant fructosamine-3 kinase, 3.33 mM ATP and 1.33 mM $MgCl_2$ and the other eye was injected with 50 ml saline. The whole eyes were then stored at 37° C. for 24 hours in NaCl 0.9% and lenses were dissected under the microscope. During dissection, the lens capsule was removed as well as the fibers at the zonula and lenses were rinsed with NaCl 0.9% to remove black pigmentary cells, blood cells and debris, to allow maximal comparison in appreciation of the color of the lens and measurements by near-infrared spectroscopy. Lenses were also prepared for histological studies. As is shown in FIG. 2*a*, a discoloration and a transition from cloudy to clear of the treated eye occurred. FIG. 3 further demonstrates that the extension rate upon the same force is higher for the treated lens when compared to the untreated lens.

Example 3

Figure 2B:
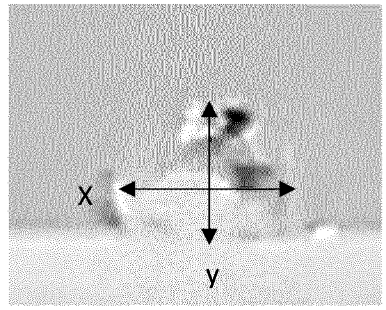
FIG. 2*b* shows the macroscopic changes in mice lenses. Following fructosamine-3-kinase treatment a striking change in lens geometry (depicted by the x/y axis ratio) is observed. Following treatment, the spherical geometry is restored.
Figure 2B:
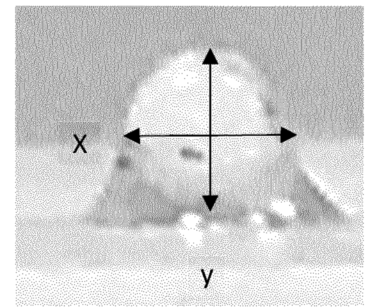
Figure 2B:
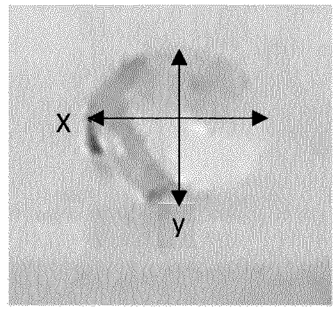
Figure 2B:
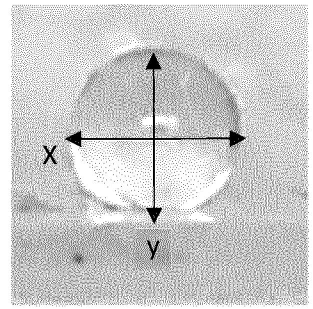
Figure 4:
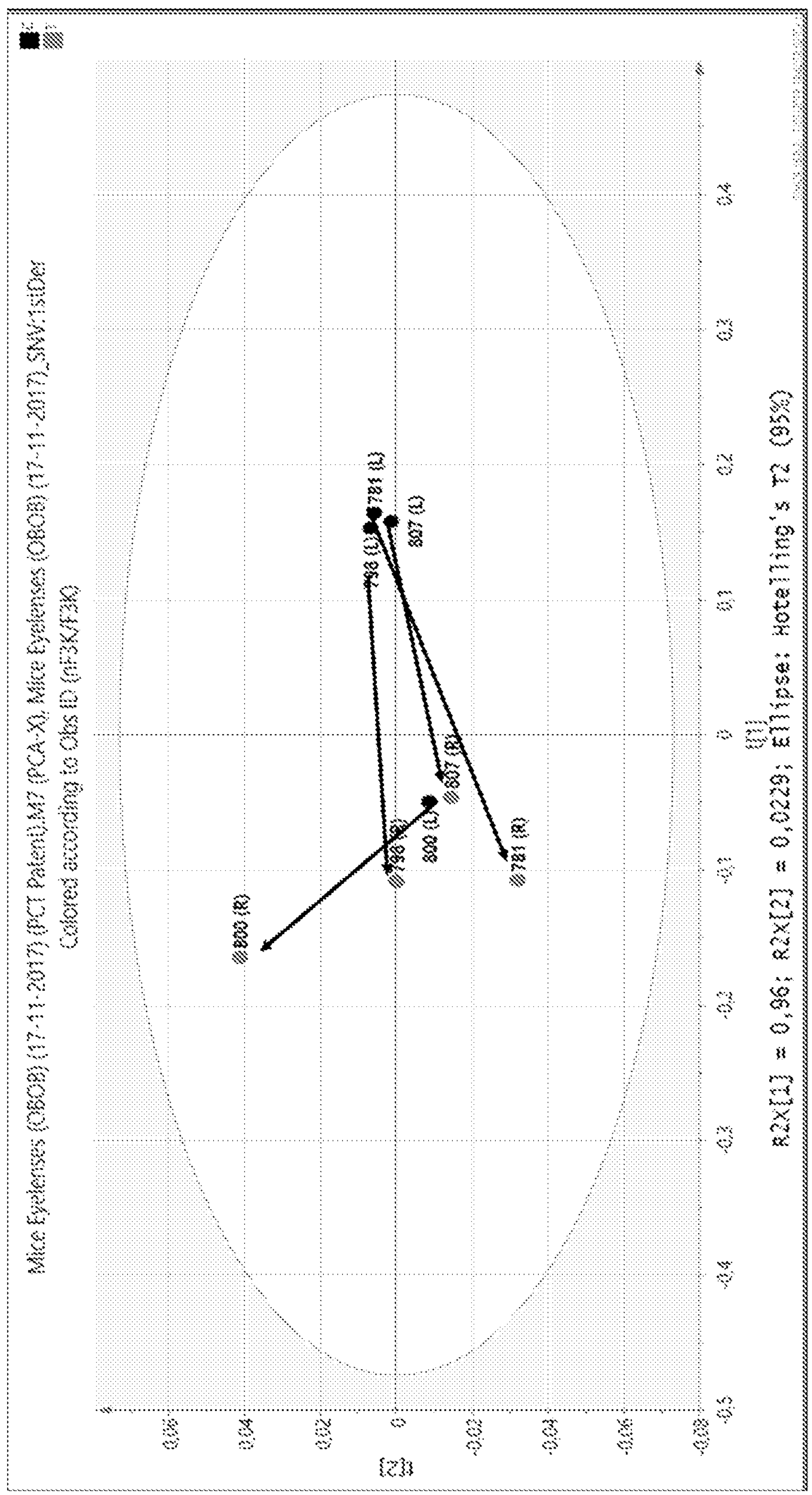
FIG. 4 shows the principle component analysis based on infrared spectral changes of ob/ob mice lenses following intravitreal treatment with recombinant fructosamine-3 kinase in vivo. A mixture of 12.5 pg/mL of recombinant fructosamine-3 kinase, 2.5 mM ATP and 0.5 mM $MgCl_2$ was injected in the right eye (R) of each mouse, whereas the left eye (L) was injected with saline. After 24 h incubation, mice were sacrificed and eyes were enucleated. Lenses were dissected and analyzed for spectral changes with near-infrared spectroscopy. Arrows indicate the difference between the saline treated (C, light grey) and contralateral fructosamine-3 kinase treated (T, dark grey) eyes of each mouse. All mice used in this experiment were ob/ob mice.

Monitoring Deglycation Following Treatment in Mice wt/wt and ob/ob mice from 36-38 weeks old were anesthetized during the surgical procedure with inhalation anesthesia (isoflurane 5%). Both eyes of the same animal were injected, one with 5 microliter fructosamine-3 kinase (same preparation as experiment in example 2) and one with 5 microliter NaCl 0.9%. 24 hours later, mice were sacrificed and both eyes were enucleated. As depicted in FIG. 2*b*, treatment with fructosamine-3 kinase resulted in a normalization of lens geometry (the physiological spherical shape was restored). Near infrared (NIR) spectra of treated and control whole lenses were recorded off-line using a NIR spectrometer equipped with an immobilized reflection probe of seven 400 pm fibers, an InGaAs detector and a halogen lamp (AvaSpecNIR256-2.5-HSC with an FCR-7UVIR400-2-BX reflection probe, Avantes). As glycation results in a spectral shift in the near-infrared spectrum of proteins, it is possible to observe specific peak sharpening and spectral variations in NIR spectra due to deglycation of crystallins. This allows us to distinguish fructosamine-3-kinase-treated from untreated diabetic lenses. In FIG. 4, the results of the contralateral control lens (C) and the treated lens (T) are shown. This plot nicely illustrates that the use of non-invasive NIR monitoring enables us to assess the treatment in a non-destructive way.

Example 4

Deglycation of Human Lens Fragments

Fluman lens fragments were obtained following phacoemulsification during cataract surgery. Post-surgery, the conservation fluid containing the lens fragments was centrifuged at 3000 rpm for 10 minutes at room temperature. Following centrifugation the supernatant was removed. The pellets of 7 cataract patients were pooled to obtain a considerable amount of lens fragments, which could then be aliquoted. To 150 pi lens suspension aliquots were added either 100 pi deionized water (control) or 100 pi of a solution containing 8.33 pg/ml recombinant fructosamine-3 kinase, 3.33 mM ATP and 1.33 mM $MgCl_2$ (treatment) for 2 hours at 37° C. Afterwards, 1 ml of nitro blue tetrazolium reagent was added to assay the fructosamine content of the lens tissue and samples were incubated for 1 h at 37° C. in 10 mm cuvettes. Absorbance at 510, 530 and 550 nm was recorded using a Shimadzu UV-1800 spectrophotometer. After baseline correction based on the absorbance at 510 nm and 550 nm, the absorbance at 530 nm showed a 30% reduction of fructosamine content after 2 hours of fructosamine-3 kinase treatment at 37° C.

Example 5

Monitoring In Vitro Glycation and Deglycation of Mouse Lenses

Figure 5:
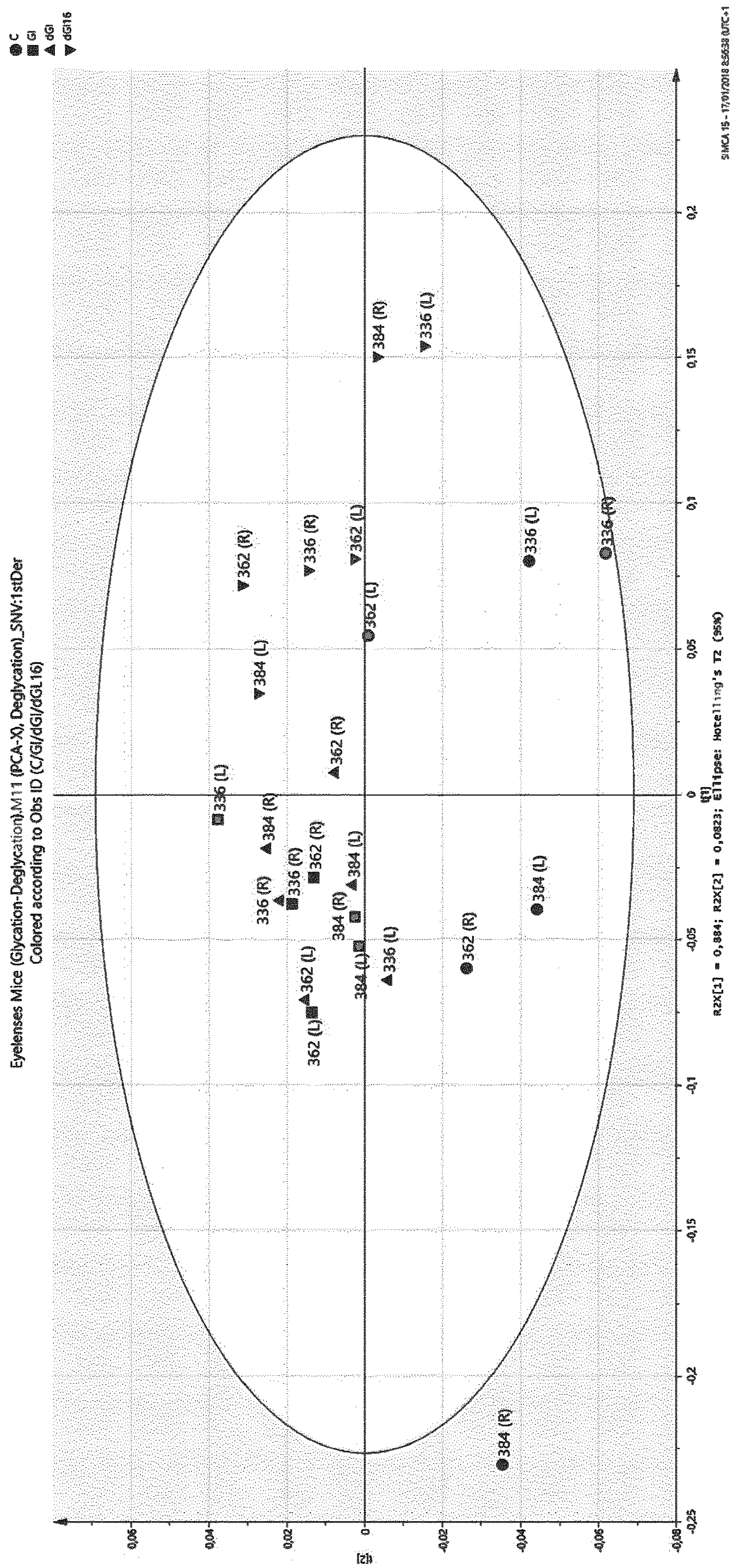
FIG. 5 shows the principle component analysis based on infrared spectral changes of mice lenses following in vitro glycation and treatment with recombinant fructosamine-3 kinase. For this experiment, wt/wt mice were used. A mixture of 8.33 pg/mL of recombinant fructosamine-3 kinase, 3.33 mM ATP and 1.33 mM $MgCl_2$ was injected in the right eye (R) of each mouse, whereas the left eye (L) was injected was saline. After 24 h incubation mice were sacrificed and eyes were enucleated. Lenses were dissected and were treated as follows: C (circle): not glycated in vitro (control); GL (square): glycated in vitro in a 10% glucose solution for 48 h at 37° C.; dGL (triangle): deglycated by in vitro treatment with 50 ml of a solution containing 8.33 pg/ml recombinant fructosamine-3 kinase, 3.33 mM ATP and 1.33 mM $MgCl_2$ for 2 h at 37° C.; dGL16 (diamond): deglycated by in vitro treatment with 50 ml of a solution containing 8.33 pg/ml recombinant fructosamine-3 kinase, 3.33 mM ATP and 1.33 mM $MgCl_2$ for 16 h at 37° C. L: left eye; R: right eye. Spectra at 1375-1515 nm (7272-6600 cm 1) and 1650-1730 nm (6060-5780 cm 1) were merged.
Figure 6:
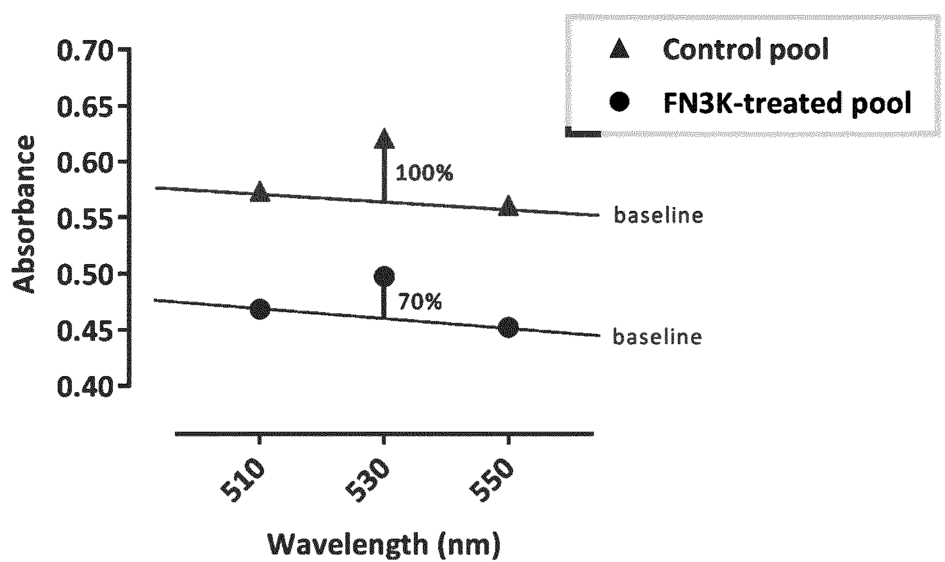
FIG. 6 shows deglycation upon fructosamine-3 kinase treatment of human lens fragments. A pool of human lens fragments of 7 cataract patients was aliquoted and treated with either deionized water (control) or a solution containing 8.33 pg/ml recombinant fructosamine-3 kinase, 3.33 mM ATP and 1.33 mM $MgCl_2$ (FN3K-treatment) for 2 hours at 37° C. Fructosamine content of the lens tissue was assayed using a nitro blue tetrazolium reagent. Absorbance at 510, 530 and 550 nm was recorded using a Shimadzu UV-1800 spectrophotometer.

Changes in the near-infrared spectrum of mouse lenses are observed upon in vitro glycation and treatment with recombinant fructosamine-3 kinase. Both eyes of wt mice were eviscerated and enucleated. The mouse eye lenses were glycated in vitro in a 10% glucose solution for 48 h at 37° C. and deglycated afterwards by immersion in 50 ml of a solution containing 8.33 pg/ml recombinant fructosamine-3 kinase, 3.33 mM ATP and 1.33 mM $MgCl_2$ for 16 hours at 37° C. Glycation was monitored by recording near-infrared spectra before and after glycation and after 2 and 16 hours of treatment. Principal component analysis of the merged spectra at 1375-1515 nm (7272-6600 cm 1) and 1650-1730 nm (6060-5780 cm 1) shows a population shift to the left upon in vitro glycation (FIG. 5) and a shift in the opposite direction upon fructosamine-3 kinase treatment. The shift is dependent on the incubation time with the enzyme, furthermore indicating its possibly deglycating effect.

Example 6 macroscopic changes of lenses of pig, sheep and horse observed following overnight treatment with intravitreal injection of fructosamine-3 kinase and an ATP generating system.

To limit the concentration of ATP present in the mixture injected, an ATP regeneration system is employed using, for example, phosphocreatine as a secondary energy source and creatine kinase to transfer its phosphate group to ADP to regenerate ATP (11, 12,13).

Fructosamine-3-kinase activity is measured in the presence of a range of 0.1 to 1000 mM of ATP and with or without a tenfold excess of phosphocreatine (Sigma-Aldrich, The Netherlands). To regenerate ATP, 500 pg/ml creatine kinase (such as recombinant human creatine kinase BB (Biotechne R&D Systems Europe, UK) or rabbit muscle creatine kinase (Sigma)) is added. In an in vitro microtiter kinase activity assay (R&D Systems) with a 1-deoxy-1-morpholino-D-fructose substrate (DMF, Biotechne R&D Systems Europe, UK), ADP released after FN3K activity was converted to free phosphate by a phosphatase and phosphate release was measured. In presence of 4 pg/ml FN3K, phosphate release was dependent on the ATP concentration (0.04-2.4 mM) added. However, if an ATP regeneration system consisting of 20 mM phosphocreatine (Sigma) and 0.5 mg/ml creatine kinase from rabbit muscle (Sigma) was added to the mixture, phosphate release decreased, indicating activity of the ATP regenerating system. An HPLC-based activity assay for FN3K with the substrate N-a-hippuryl-N-e-psicosyllysine (14) demonstrates that the ATP concentration required for FN3K activity lowers upon addition of an ATP regeneration system.

Figure 7A:
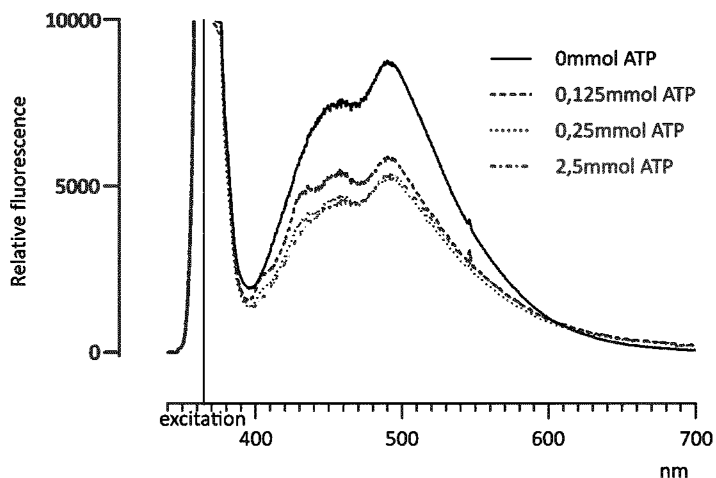
FIG. 7A shows the decrease in fluorescent glycated compounds upon treatment with FN3K supplemented with sufficient (0.25-2.5 mM) or limiting (0.125 mM) ATP.
Figure 7B:
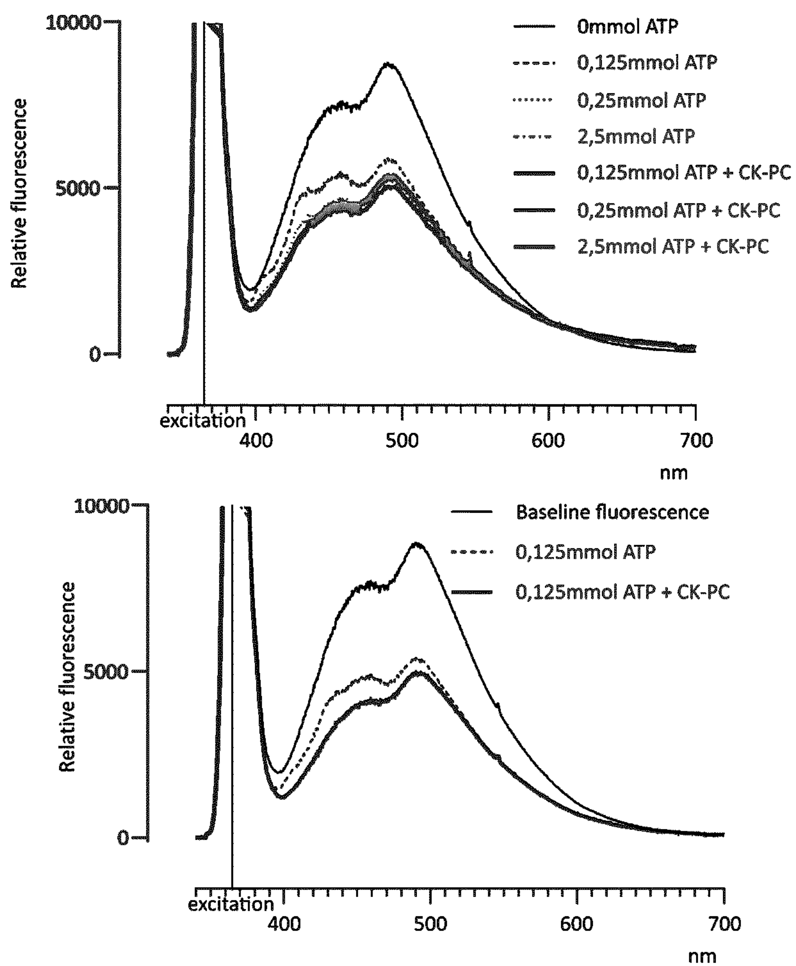
FIG. 7B shows a decrease in fluorescence of FN3K-treated samples supplemented with limiting (0.125 mM) ATP in absence or presence of an ATP regeneration system (CK-PC), in two independent experiments.

To demonstrate the use of an ATP-regeneration system to enhance FN3K treatment in human lenses, twenty human cataract lenses were fragmented by phacoemulsification and pooled. Human cataract lens fragment pool samples were treated with a solution of 16 pg/ml FN3K, 4 mM $MgCl_2$ and 0, 0.125, 0.25 or 2.5 mM ATP in saline, either as such or supplemented with an ATP regeneration system consisting of 20 mM phosphocreatine (Sigma) and 0.5 mg/ml creatine kinase from rabbit muscle (Sigma), which was activated in 20 mM DTT prior to use according to Favre et al. (15). Fluorescent spectra were recorded off-line using a Flame-S—VIS-NIR-ES spectrometer equipped with an immobilized reflection probe of seven 400 pm fibers and a LLS-365 high power LED light source (Flame-S—VIS-NIR-ES with QR400-7-VIS-BX Premium reflection probe, OceanOptics). Excitation intensity was set as such that the detected 365 nm peak (excitation beam) was equally high in each condition measured, allowing comparison of spectra. Fluorescence peaks at 455 nm and 490 nm lowered upon FN3K treatment (FIG. 7A), indicating a decrease in glycated compounds. If the ATP concentration was limiting (0.125 mM), however, fluorescence decrease was limited. Upon addition of an ATP regeneration system (FIG. 7B left), this effect was reversed and fluorescence at 455 nm and 490 nm decreased to levels similar to FN3K-treated samples with sufficient (0.25-2.5 mM) ATP added, whereas fluorescence levels of the latter did not change upon addition of the ATP regeneration system. In an independent repeat experiment (FIG. 7B right), a similar ATP regeneration system-induced decrease of fluorescence was observed upon FN3K treatment with a limiting ATP concentration (0.125 mM). These results indicate that if ATP-concentrations are limiting, FN3K-treatment of cataractous human lens fragments can be enhanced by addition of an ATP-regeneration system consisting, for example, of 20 mM phosphocreatine (Sigma) and 0.5 mg/ml creatine kinase.

Considering that the KM of fructosamine-3-kinase for ATP might vary with the substrate used (DMF versus natural substrates such as fructosamine (16, 17)) and the requirement for diffusion from the intravitreal space to the lens, 12.5 pg/ml fructosamine-3-kinase is injected intravitreally in a reaction mixture containing 1 to 1000 mM ATP and a tenfold excess of phosphocreatine, 50 pg/ml creatine kinase and 1 mM $MgCl_2$ in HEPES-buffered saline pH 8.0.

Macroscopic changes of cattle lenses are observed following overnight treatment with the abovementioned treatment mixture. Two eyes of the same animal are eviscerated and compared to have the best comparable material possible. The eyes are eviscerated from fresh cadavers and transported to the lab on ice before injection. One eye is injected with a final concentration of 12.5 pg/ml fructosamine-3-kinase in a reaction mixture as described above, whereas the second eye is injected with the same reaction mixture but fructosamine-3-kinase is omitted. The whole eyes are incubated at 37° C. for 24 hours in sterile 0.9% NaCl and lenses are dissected under the microscope. During dissection, the lens capsule is removed, as well as the fibers at the zonula and lenses are rinsed with sterile 0.9% NaCl to remove black pigmentary cells, blood cells and debris, so that a maximal comparison in appreciation of the color of the lens and measurements by near-infrared spectroscopy were possible. Lenses are also prepared for histological studies.

REFERENCES

1. Liu Y C, Wilkins M, Kim T, Malyugin B, Mehta J S. Cataracts. Lancet 2017; 50140-6736(17)30544-5.
2. www.who.int/blindness/causes/prioritv/en/inclexl.html.
3. Agarwal A, Jacob S. Current and effective advantages of femto phacoemulsification. Curr Opin Ophthalmol 2017; 28:49-5.
4. Shiels A, Hejtmancik J F. Genetics of human cataract. Clin Genet 2013; 84:120-127.
5. Dillon J, Skonieczna M, Mandal K, Paik D. The photochemical attachment of the O-glucoside of 3-hydroxykynurenine to alpha-crystallin: a model for lenticular aging. Photochem Photobiol 1999; 69:248-53.
6. Avila F, Sebastian T, Baraibar M A, Friguet B, Silva E. Photosensitized reactions mediated by the major chromophore arising from glucose decomposition, result in oxidation and cross-linking of lens proteins and activation of the proteasome. Biochim. Biophys. Acta 2012; 1822: 564-572.
7. Pescosolido N, Barbato A, Giannotti R, Komaiha C, Lenarduzzi F. Age-related changes in the kinetics of human lenses: prevention of the cataract. Int J Ophthalmol 2016; 9:1506-1517.
8. Delpierre G, Collard F, Fortpied J, Van Schaftingen E. Fructosamine 3-kinase is involved in an intracellular deglycation pathway in human erythrocytes. Biochem J 2002; 365:801-8.
9. Rosenfeld P J, Brown D M, Heier J S, Boyer D S, Kaiser P K, Chung C Y, Kim RY, for the MARINA Study Group. Ranibizumab for neovascular age-related macular degeneration. N Engl J Med 2006; 355:1419-31.
10. Halfter W, Dong S, Schurer B, Ring C, Cole G J, Eller A. Embryonic synthesis of the inner limiting membrane and vitreous body. Invest Ophthalmol Vis Sci 2005; 46:2202-9.
11. Ryan D. Woodyer, Tyler Johannes, and Huimin Zhao, “Regeneration of Cofactors for Enzyme Biocatalysis in Enzyme Technology,” in Enzyme Technology (Springer Science+Business Media, Inc. and Asiatech Publishers, Inc., 2006).
12. Andexer J N & Richter M (2015) Emerging Enzymes for ATP Regeneration in Biocatalytic Processes. ChemBioChem 16: 380-386.
13. Hayer-Hartl M (2000) Assay of Malate Dehydrogenase. In Chaperonin Protocols pp 127-132. Springer, Totowa, N.J. Available at: link springer com/protocol/10.1385/1-59259-061-6.127 [Accessed Nov. 26, 2017]
14. Hellwig, A., Scherber, A., Koehler, C., Hanefeld, M., and Henle, T. (2014). A new HPLC-based assay for the measurement of fructosamine-3-kinase (FN3K) and FN3K-related protein activity in human erythrocytes. Clin. Chem. Lab. Med. 52, 93-101.
15. Favre, D., and Muellhaupt, B. (2005). Reactivation of creatine kinase by dithiothreitol prior to use in an in vitro translation extract. ALTEX 22, 259-264.
16. Delpierre G, Rider M H, Collard F, Stroobant V, Vanstapel H & Santos E (2000) Identification, cloning, and heterologous expression of a mammalian fructosamine-3-kinase. Diabetes 49: 1627-1634.
17. Szwergold B S, Howell S & Beisswenger P J (2001) Human fructosamine-3-kinase: purification, sequencing, substrate specificity, and evidence of activity in vivo. Diabetes 50: 2139-2147.

The invention claimed is:

1. A composition comprising:

a fructosamine-3-kinase, and adenosine triphosphate (ATP) and/or an ATP regenerating system, in amounts useful to treat a cataract in a human or an animal subject, wherein the composition is configured for intravitreal injection into the subject.

2. The composition of claim 1, further comprising magnesium ions.

3. The composition of claim 1, wherein the fructosamine-3-kinase is a recombinant fructosamine-3-kinase.

4. The composition of claim 3, wherein the recombinant fructosamine-3-kinase is produced by a recombinant production method in *Pichia pastoris*.

5. The composition of claim 4, wherein the recombinant fructosamine-3-kinase has an amino acid sequence of SEQ ID NO:1 or SEQ ID NO:2.

6. A method of treating a human or animal subject having a cataract, the method comprising:

administering to the subject a composition comprising a fructosamine-3-kinase and adenosine tri phosphate (ATP)

so as to treat the subject's cataract.

7. The method according to claim 6, wherein the composition is administered by intravitreal injection.

8. The method according to claim 6, wherein the composition further comprises magnesium ions.

9. The method according claim 6, wherein the composition further comprises an adenosine triphosphate regenerating system.

10. The method according to claim 6, wherein the fructosamine-3-kinase is a recombinant fructosamine-3-kinase.

11. The method according to claim 10, wherein the recombinant fructosamine-3-kinase is produced by recombinant production in *Pichia pastoris*.

12. The method according to claim 11, wherein the recombinant fructosamine-3-kinase comprises an amino acid sequence as given by SEQ ID NO:1 or SEQ ID NO:2.

13. The method according to claim 11, wherein the recombinant fructosamine-3-kinase has an amino acid sequence of SEQ ID NO:1 or SEQ ID NO:2.

14. The method according to claim 6, wherein the treatment of cataract involves a deglycation of lens proteins resulting in clearing and softening of the subject's lens.

15. A method for treating a human or animal subject having a cataract, the method comprising:

administering to the subject a composition comprising a fructosamine-3-kinase and an adenosine triphosphate regenerating system so as to treat the cataract.

16. The method according to claim 15, wherein the composition is administered by intravitreal injection.

17. The method according to claim 15, wherein the composition further comprises magnesium ions.

18. The method according to claim 15, wherein the fructosamine-3-kinase is a recombinant fructosamine-3-kinase.

19. The method according to claim 15, wherein the treatment of the cataract involves a deglycation of lens proteins resulting in clearing and softening of the subject's lens.

* * * * *

SEQUENCE LISTING

```
<160> NUMBER OF SEQ ID NOS: 4

<210> SEQ ID NO 1
<211> LENGTH: 325
<212> TYPE: PRT
<213> ORGANISM: Homo sapiens

<400> SEQUENCE: 1

Met His His His His His His Val Asn Gly Pro Gly Ser Asp Glu Val
1               5                   10                  15

Asp Glu Gln Leu Leu Arg Ala Glu Leu Arg Thr Ala Thr Leu Arg Ala
            20                  25                  30
```

```
Phe Gly Gly Pro Gly Ala Gly Cys Ile Ser Glu Gly Arg Ala Tyr Asp
        35                  40                  45

Thr Asp Ala Gly Pro Val Phe Val Lys Val Asn Arg Arg Thr Gln Ala
    50                  55                  60

Arg Gln Met Phe Glu Gly Glu Val Ala Ser Leu Glu Ala Leu Arg Ser
65                  70                  75                  80

Thr Gly Leu Val Arg Val Pro Arg Pro Met Lys Val Ile Asp Leu Pro
                85                  90                  95

Gly Gly Gly Ala Ala Phe Val Met Glu His Leu Lys Met Lys Ser Leu
            100                 105                 110

Ser Ser Gln Ala Ser Lys Leu Gly Glu Gln Met Ala Asp Leu His Leu
        115                 120                 125

Tyr Asn Gln Lys Leu Arg Glu Lys Leu Lys Glu Glu Glu Asn Thr Val
    130                 135                 140

Gly Arg Arg Gly Glu Gly Ala Glu Pro Gln Tyr Val Asp Lys Phe Gly
145                 150                 155                 160

Phe His Thr Val Thr Cys Cys Gly Phe Ile Pro Gln Val Asn Glu Trp
                165                 170                 175

Gln Asp Asp Trp Pro Thr Phe Phe Ala Arg His Arg Leu Gln Ala Gln
            180                 185                 190

Leu Asp Leu Ile Glu Lys Asp Tyr Ala Asp Arg Glu Ala Arg Glu Leu
        195                 200                 205

Trp Ser Arg Leu Gln Val Lys Ile Pro Asp Leu Phe Cys Gly Leu Glu
    210                 215                 220

Ile Val Pro Ala Leu Leu His Gly Asp Leu Trp Ser Gly Asn Val Ala
225                 230                 235                 240

Glu Asp Asp Val Gly Pro Ile Ile Tyr Asp Pro Ala Ser Phe Tyr Gly
                245                 250                 255

His Ser Glu Phe Glu Leu Ala Ile Ala Leu Met Phe Gly Gly Phe Pro
            260                 265                 270

Arg Ser Phe Phe Thr Ala Tyr His Arg Lys Ile Pro Lys Ala Pro Gly
        275                 280                 285

Phe Asp Gln Arg Leu Leu Leu Tyr Gln Leu Phe Asn Tyr Leu Asn His
    290                 295                 300

Trp Asn His Phe Gly Arg Glu Tyr Arg Ser Pro Ser Leu Gly Thr Met
305                 310                 315                 320

Arg Arg Leu Leu Lys
                325


<210> SEQ ID NO 2
<211> LENGTH: 308
<212> TYPE: PRT
<213> ORGANISM: Homo sapiens

<400> SEQUENCE: 2

Glu Gln Leu Leu Arg Ala Glu Leu Arg Thr Ala Thr Leu Arg Ala Phe
1               5                   10                  15

Gly Gly Pro Gly Ala Gly Cys Ile Ser Glu Gly Arg Ala Tyr Asp Thr
            20                  25                  30

Asp Ala Gly Pro Val Phe Val Lys Val Asn Arg Arg Thr Gln Ala Arg
        35                  40                  45

Gln Met Phe Glu Gly Glu Val Ala Ser Leu Glu Ala Leu Arg Ser Thr
    50                  55                  60

Gly Leu Val Arg Val Pro Arg Pro Met Lys Val Ile Asp Leu Pro Gly
65                  70                  75                  80
```

```
Gly Gly Ala Ala Phe Val Met Glu His Leu Lys Met Lys Ser Leu Ser
            85                  90                  95

Ser Gln Ala Ser Lys Leu Gly Glu Gln Met Ala Asp Leu His Leu Tyr
            100                 105                 110

Asn Gln Lys Leu Arg Glu Lys Leu Lys Glu Glu Glu Asn Thr Val Gly
        115                 120                 125

Arg Arg Gly Glu Gly Ala Glu Pro Gln Tyr Val Asp Lys Phe Gly Phe
    130                 135                 140

His Thr Val Thr Cys Cys Gly Phe Ile Pro Gln Val Asn Glu Trp Gln
145                 150                 155                 160

Asp Asp Trp Pro Thr Phe Phe Ala Arg His Arg Leu Gln Ala Gln Leu
            165                 170                 175

Asp Leu Ile Glu Lys Asp Tyr Ala Asp Arg Glu Ala Arg Glu Leu Trp
            180                 185                 190

Ser Arg Leu Gln Val Lys Ile Pro Asp Leu Phe Cys Gly Leu Glu Ile
        195                 200                 205

Val Pro Ala Leu Leu His Gly Asp Leu Trp Ser Gly Asn Val Ala Glu
    210                 215                 220

Asp Asp Val Gly Pro Ile Ile Tyr Asp Pro Ala Ser Phe Tyr Gly His
225                 230                 235                 240

Ser Glu Phe Glu Leu Ala Ile Ala Leu Met Phe Gly Gly Phe Pro Arg
            245                 250                 255

Ser Phe Phe Thr Ala Tyr His Arg Lys Ile Pro Lys Ala Pro Gly Phe
            260                 265                 270

Asp Gln Arg Leu Leu Leu Tyr Gln Leu Phe Asn Tyr Leu Asn His Trp
        275                 280                 285

Asn His Phe Gly Arg Glu Tyr Arg Ser Pro Ser Leu Gly Thr Met Arg
    290                 295                 300

Arg Leu Leu Lys
305
```

<210> SEQ ID NO 3
<211> LENGTH: 978
<212> TYPE: DNA
<213> ORGANISM: Homo sapiens

<400> SEQUENCE: 3

```
atgcatcatc atcatcatca tgttaacggt ccaggttctg atgaagttga tgaacagttg     60

ttgagagctg agttgagaac tgctactttg agagcttttg gtggtccagg tgctggttgt    120

atttctgagg gtagagctta cgatactgac gctggtccag ttttcgttaa ggttaacaga    180

agaactcagg ctagacagat gttcgagggt gaagttgctt ctttggaggc tttgagatcc    240

actggtttgg ttagagttcc aagaccaatg aaggttatcg acttgccagg tggtggtgct    300

gcttttgtta tggaacactt gaagatgaag tccttgtcct cccaggcttc taagttgggt    360

gaacaaatgg ctgacttgca cttgtacaac cagaagttga gagaaaagtt gaaagaggaa    420

gagaacactg ttggtagaag aggtgaaggt gctgagccac aatacgttga caagttcggt    480

ttccacactg ttacttgttg tggtttcatc ccacaggtta acgagtggca agatgactgg    540

ccaactttct tcgctagaca cagattgcaa gctcagttgg acttgatcga gaaggactac    600

gctgacagag aagctagaga attgtggtcc agattgcagg ttaagatccc agacttgttc    660

tgtggtttgg agatcgttcc agctttgttg cacggtgatt tgtggtctgg taacgttgct    720

gaagatgacg ttggtccaat tatctacgac ccagcttctt tctacggtca ctctgaattc    780
```

```
gagttggcta tcgctttgat gttcggtggt ttcccaagat ccttcttcac tgcttaccac    840

agaaagatcc caaaggctcc aggtttcgac cagagattgt tgttgtacca gttgttcaac    900

tacttgaacc attggaacca cttcggtaga gagtacagat ctccatcctt gggtactatg    960

agaagattgt tgaagtaa                                                  978


<210> SEQ ID NO 4
<211> LENGTH: 927
<212> TYPE: DNA
<213> ORGANISM: Homo sapiens

<400> SEQUENCE: 4

gaacagttgt tgagagctga gttgagaact gctactttga gagcttttgg tggtccaggt     60

gctggttgta tttctgaggg tagagcttac gatactgacg ctggtccagt tttcgttaag    120

gttaacagaa gaactcaggc tagacagatg ttcgagggtg aagttgcttc tttggaggct    180

ttgagatcca ctggtttggt tagagttcca agaccaatga aggttatcga cttgccaggt    240

ggtggtgctg cttttgttat ggaacacttg aagatgaagt ccttgtcctc ccaggcttct    300

aagttgggtg aacaaatggc tgacttgcac ttgtacaacc agaagttgag agaaaagttg    360

aaagaggaag agaacactgt tggtagaaga ggtgaaggtg ctgagccaca atacgttgac    420

aagttcggtt tccacactgt tacttgttgt ggtttcatcc cacaggttaa cgagtggcaa    480

gatgactggc caactttctt cgctagacac agattgcaag ctcagttgga cttgatcgag    540

aaggactacg ctgacagaga agctagagaa ttgtggtcca gattgcaggt taagatccca    600

gacttgttct gtggtttgga gatcgttcca gctttgttgc acggtgattt gtggtctggt    660

aacgttgctg aagatgacgt tggtccaatt atctacgacc cagcttcttt ctacggtcac    720

tctgaattcg agttggctat cgctttgatg ttcggtggtt tcccaagatc cttcttcact    780

gcttaccaca gaaagatccc aaaggctcca ggtttcgacc agagattgtt gttgtaccag    840

ttgttcaact acttgaacca ttggaaccac ttcggtagag agtacagatc tccatccttg    900

ggtactatga gaagattgtt gaagtaa                                        927
```